United States Patent [19]

Fink

[11] Patent Number: 4,913,309

[45] Date of Patent: Apr. 3, 1990

[54] DISPOSAL CONTAINER AND TRANSPORT CASE FOR INFECTIOUS AND HAZARDOUS WASTE MATERIAL

[76] Inventor: James J. Fink, 700 N. Fifth St., Cannon Falls, Minn. 55009

[21] Appl. No.: 207,722

[22] Filed: Jun. 16, 1988

[51] Int. Cl.⁴ .............................................. B65D 90/04
[52] U.S. Cl. .................................... 220/404; 220/254; 220/460
[58] Field of Search ............... 220/403, 404, 460, 461, 220/468, 345, 351, 254

[56] References Cited

U.S. PATENT DOCUMENTS

696,832 4/1902 Mascble .......................... 220/460 X
3,675,810 7/1972 Nors, Jr. et al. ................. 220/254 X

Primary Examiner—John Fox
Attorney, Agent, or Firm—Moore & Hansen

[57] ABSTRACT

A disposal container comprising a generally rectangular body portion defining a receptacle with an open top bounded by a rim, and a lid member which is slidably and engagingly mounted over the top of the rim of the container body. The lid member is secured to the container body using a tamper evidencing locking strips. The lid member has a convex raised top surface with a centrally located upwardly projecting cylindrical neck region defining a generally circular aperture. The aperture is selectively sealed by a plastic plug having a concave, recessed interior. The lid member has an pivotably mounted carrying handle, and the entire disposal container may be seated within a mounting bracket which is attached to a wall or vehicle.

21 Claims, 3 Drawing Sheets

DISPOSAL CONTAINER AND TRANSPORT CASE FOR INFECTIOUS AND HAZARDOUS WASTE MATERIAL

BACKGROUND OF THE INVENTION

This invention relates generally to devices for disposing of used medical equipment or waste materials, and particularly to a method and apparatus for the containment, transportation, and safe disposal of biologically infectious or potentially hazardous waste materials.

The disposal of used medical or research equipment has always presented certain problems These items may include contaminated syringes and needles, scalpels, blades, glass medication or drug dispensing ampules, intravenous sets, blood specimen containers, bandages and pads, surgical gloves, and many hundreds of other assorted instruments and supplies. Those items having pointed ends, such as syringes or needles, scalpels, blades, and other supplies capable of accidentally puncturing the skin or protective garments, have become known as "sharps."

The variety of such items has been steadily increasing over recent years and because disposability is a primary requirement for almost all medical supplies, the sheer number of such items being disposed of has also increased. These items are often contaminated—or must be treated as if contaminated—by an unknown variety of infectious or hazardous agents.

While it is accepted practice to separate radioactively contaminated waste from infectious or other hazardous wastes, it is often the case that radioactive wastes, infectious substances, viral or other biological contaminants, blood or tissue samples, unused medications, mutagenic compounds, and a host of other potential health hazards are disposed of together in common receptacles. The combining of such wastes creates additional problems, since any one may be more dangerous when in combination with another, and because it eliminates any chance for personnel to later identify what hazardous items may be in each receptacle.

Because many of these items are being used in medical facilities and research laboratories under conditions where the personnel must concentrate on a particular emergency at hand, where their activities are hampered by working in a sterile negative-pressure hood or other protective equipment, or must concentrate on performing many repetitive activities within a given time period, the disposal devices for such items must be made as safe, easy to use, and as relatively trouble or error free as possible.

Members of the medical community working with patients or in research facilities where communicable diseases such as Hepatitis-B, Staphylococcus, and the like may be present have shown considerable concern over the possible transmission of those communicable diseases through the accidental exposure to contaminated supplies, particularly to sharps. This concern has grown considerably in recent years, not just among those who routinely work with communicable diseases, but throughout the medical and public service sectors, due predominantly to widespread recognition of the increase in acquired immune deficiency syndrome (AIDS) cases. While there is a great deal of controversy surrounding the possible methods and likelihood of transmission of the AIDS viruses, it is well accepted that accidental contact with contaminated sharps presents one of the most dangerous threats of unintentional exposure to the AIDS virus for medical personnel.

It is important that the various types of wastes be disposed of appropriately. Some waste must be burned, while it is particularly dangerous to burn others. Some waste must first be sterilized, while others must be biologically or chemically neutralized. Others must be disposed of in a manner which will prevent any exposure to the environment. An additional consideration for disposing of particular sharps, specifically syringes and needles which are not burned, is the ongoing problem of preventing those needles from falling into the hands of intravenous (IV) drug users once they have been disposed of, since such needles are particularly valuable and many persons resort to combing through trash bins at hospitals or medical facilities in search of such items.

The governmental and institutionally self-imposed regulations for dealing with contaminated waste materials have become quiet expansive and confusing. It is therefore more efficient and practical for medical facilities of all sizes to place the responsibility for collecting, transporting, and disposing of infectious or other hazardous wastes in the hands of qualified professionals who perform this service. Consequently, the nature of the activities performed by these services gives rise to peculiar needs and considerations for the design of their disposal containers.

In the past, a variety of receptacles and disposal containers have been designed and used for the containment and disposal of infectious or hazardous wastes.

One feature which has been incorporated into a variety of different disposal containers is the "one way" closure. The one way closure is intended to seal the otherwise open neck of a disposal container, to prevent contaminants from becoming airborne, and to prevent sharps or other waste from falling or protruding out of the disposal container. Representative examples of such one way closures on disposal containers are shown in the U.S. Pat. Nos. 4,351,434; 4,454,944; and 3,381,814. The concept of a one way closure has also been utilized in other types of waste receptacles, such as that shown in U.S. Pat. No. 3,089,633 disclosing a trash container for use in automobiles, and in other types of products such as the dispensing carton disclosed in U.S. Pat. No. 3,556,293. The closure may range anywhere from a simple slit configuration as shown in U.S. Pat. No. 4,121,755, to shapes designed specifically for the disposal of particular items such as the system shown in the U.S. Pat. No. 4,625,877 for dispensing of syringe needles, and the star-like closure configurations of the patents mentioned above. While the closure is generally positioned on the top of the disposal container, it may in some instances be positioned on the side of the container, as shown in U.S. Pat. No. 3,494,536.

While being suitable for some applications, these disposal containers present several common deficiencies.

Medical personnel often injure themselves attempting to press sharps through the one way type closure. Since the person cannot see inside the container to determine if it is full, and the closure itself restricts the size and shape of certain articles which may pass through, persons may injure themselves attempting to force an item through the closure into a full container, or one which is not designed to accommodate the particular item. If an item becomes jammed in the closure, the person must use his finger to force the item into the container, which can result in piercing that finger with contaminated sharps or other objects which are pointed upwardly in the container.

The seal provided by such one way closures is generally not air tight, and therefore not suitable for use in the sterile environment required in many research facilities. Such closures are also subject to being deformed after continued use.

Many of the containers themselves are made from lightweight and non-durable materials so they can be disposed of, but consequently do not provide a complete seal around the periphery of the container or at its folds, and will permit liquid contaminants to leak out. More durable containers designed for repeated use, such as that shown in U.S. Pat. No. 4,454,944, may be constructed such that they can be autoclaved for sterilization, but are impractical to clean or empty.

One improvement has been the inclusion of a thin plastic liner, such as shown in U.S. Pat. Nos. 4,534,489 and 3,756,574. Such a liner is not practical in a container which is deformable or foldable, however, since items shifting within the flexible walls of the container will puncture the liner, or will protrude through folds and seams. Moreover, such a liner may restrict certain items from being placed within the container unless it is held open by the container rim, which then presents problems in maintaining the liner in an upright position around that rim when filled with any weight of saturated materials, liquids, or glassware.

BRIEF SUMMARY OF THE INVENTION

It is therefore one object of this invention to design a disposal container for infectious or other hazardous wastes which is sturdy, durable, and impervious to those contaminants frequently encountered in medical or research facilities, and which may be used repeatedly to contain, transport, and dispose of infectious and other hazardous wastes, including biological and radioactive contaminants and medical sharps.

It is a related object of this invention to design the above disposal container such that it may be used either within medical and research facilities, or in the field by mobile paramedics, police, and fire or rescue personnel where contaminated medical items must be disposed of and where such disposal containers must withstand the particular rigors and environments encountered in such uses.

It is another object of this invention to design the above disposal container such that medical or research personnel may conveniently place contaminated items therein without the risk of injury or accidental contact with sharps, and exposure to the contaminants thereon.

It is a related object of this invention to design the above disposal container such that it may be securely mounted on a wall or vehicle, or rested on a table or counter top in a stable position, or elevated on a freestanding rack that would permit the disposal container to be used by personnel who must necessarily concentrate on other activities and operate the disposal container with one hand.

It is yet another object of this invention to design the above disposal container such that it may alternately be used with one or more liners of various types, and such that said liners will be securely held in place in an open position when the container is filled with saturated materials or heavy glassware.

It is an additional object of this invention to design the above disposal container such that a positive seal may be formed around the top of the container rim, and further such that if liquid contaminants are accidentally spilled onto or over to top of the container when disposing of an item, the contaminants will not accumulate in cracks or crevasses of the container.

It is a further object of this invention to design the above disposal container such that a person cannot accidentally open the top of the container, except for that portion used for disposal of contaminated items, nor intentionally open the top without evidencing that the container has been tampered with.

It is still another object of this invention to design the above disposal container such that the receptacle portion of the container has enough volume to contain the large number of contaminated items normally used in an emergency room or other treatment facility, without affecting the integrity of the disposal container.

It is a unique object of this invention to design the above disposal container such that it may be used selectively as an open top container having a normally unobstructed neck or disposal aperture, or alternately with a static closure to prevent contaminants from becoming airborne.

It is a related object of this invention to design the closure means for the disposal aperture of the container such that it may be easily gripped by a person without the risk of puncturing or tearing surgical gloves, or by a person who is holding instruments in their hands, such as a pipette holder or the like.

It is further a related object of this invention to design the above disposal container such that the closure means may be used as a tamping device for pressing items down into the container below the disposal aperture, and serve to protect the user's hands and fingers from injury by sharps and shield them from contact with contaminated items.

It is an object of this invention to design the above disposal container such that it may be easily and thoroughly emptied, cleaned, and sterilized after each use, and such that it may be easily and conveniently transported to a location where such cleaning and sterilization will be performed.

A distinct object of this invention is to design a transport case for a plurality of the disposal contains which permits a technician to conveniently carry several disposal containers to or from a remote area without the risk of spilling or exposing their contents, and to permit stacking of those transport cases.

Briefly described, the disposal container of this invention comprises a generally rectangular body portion defining a receptacle with an open top bounded by a rim, and a lid member which is slidably and engagingly mounted over the top of the rim of the container body. The lid member may further be secured to the container body using a tamper evidencing locking strip. The lid member has a convex raised top surface with an upwardly projecting neck region defining a generally circular aperture. The aperture may be selectively closed and sealed by a plastic plug having a concave, recessed interior. The lid member has an attached pivotable carrying handle, and the entire disposal container may be seated within a mounting bracket which is attached to a wall or vehicle.

The transport case comprises a large tote container with a hinged lid and integrally molded carrying handle. The handle is received within a channel formed in the bottom of alike transport case when stacked in a column. The channel forms a longitudinal wall inside the tote container, and together with a pair of transverse walls, serve to retain the disposal containers in a stable upright position within the transport case.

DESCRIPTION OF THE PREFERRED EMBODIMENT

The disposal container apparatus of this invention is shown in FIGS. 1-11 and referenced generally therein by the numeral 10.

Figure 1:
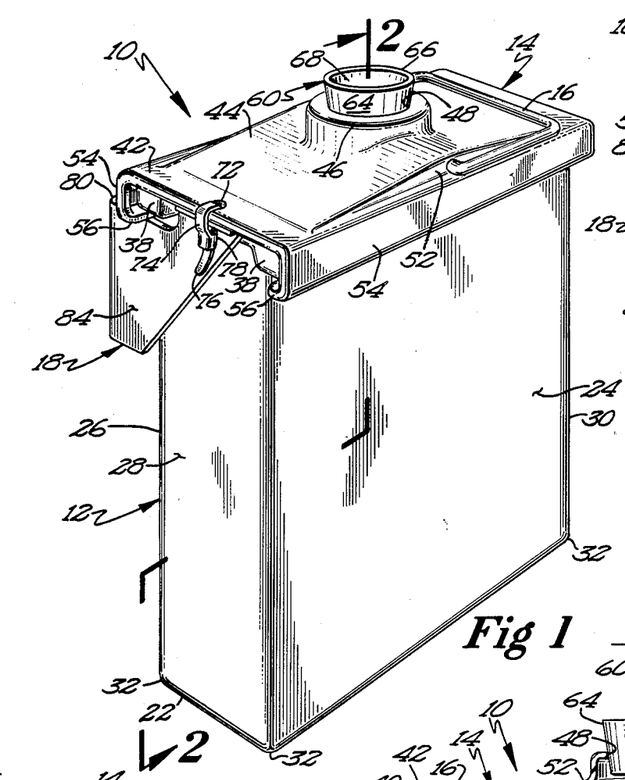
FIG. 1 is a front perspective view of the disposal container of this invention situated within its mounting bracket.

Referring particularly to FIG. 1, it may be seen that the disposal container 10 comprises a container body 12, a lid member 14 having a pivotable handle member 16, and a mounting bracket 18. The container body 12 and lid member 14 should preferably be molded from a resilient plastic resin such as 3/16th inch polyethylene, may be made opaque or translucent, and should be provided with a roughened or pebbled texture on the exterior surface thereof and with a generally smooth surface on the interior thereof. The handle member 16 should be formed from a stainless or plated metal rod. The mounting bracket 18 may be constructed from any easily cut and formed sheet metal, preferably a lightweight alloy or aluminum.

Figure 2:
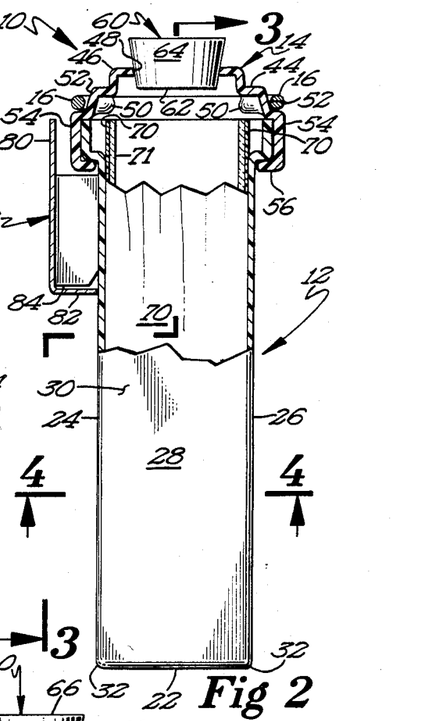
FIG. 2 is a partially sectioned side elevation view of the disposal container of this invention taken through line 2—2 of FIG. 1.
Figure 3:
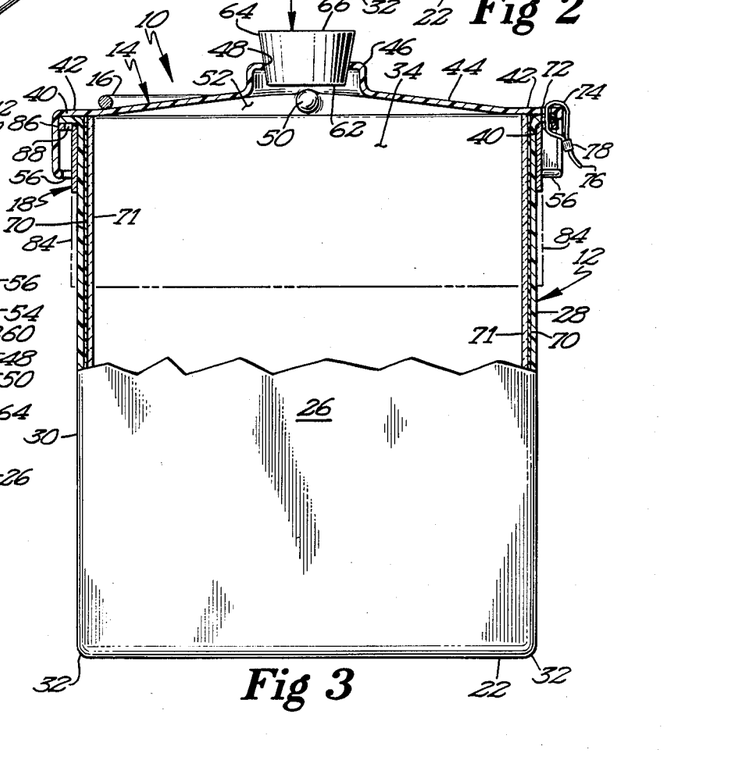
FIG. 3 is a partially sectioned rear elevation view of the disposal container of this invention taken from line 3—3 of FIG. 3.
Figure 5:
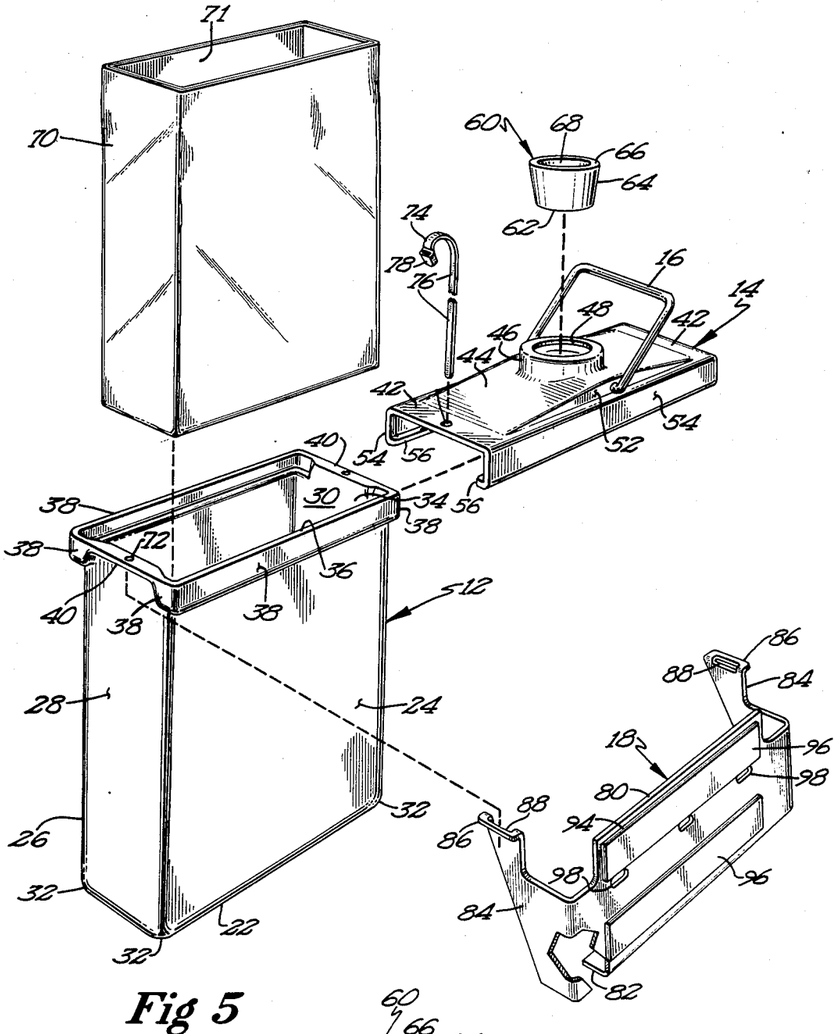
FIG. 5 is an exploded assembly view of the disposal container body, lid, liners, and mounting bracket of this invention.
Figure 6:
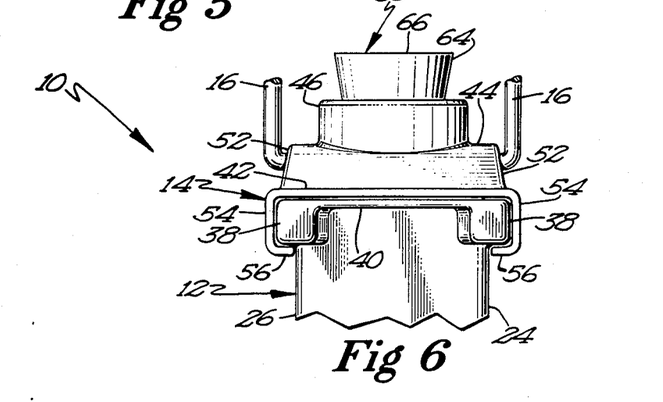
FIG. 6 is a side elevation view of the top of the disposal container of this invention showing the lid mounted on the container body.

Referring particularly to FIGS. 2, 3, and 5, it may be seen that the container body 12 consists of a generally planar, rectangular base section 22 defining the width and length of the bottom of the disposal container 10.

Extending upwardly from each edge of the base section 22 and connected thereto or molded integrally therewith are a front wall section 26, a back wall section 24, and a pair of opposing side wall sections 28, 30. The corners 32 between the base section 22 and the wall sections 24, 26, 28, 30 as well as between the wall sections 24, 26, 28, 30 themselves, should be rounded slightly.

The container body 12 also defines a receptacle region 34 situated above the base panel 22 and between the opposing wall sections 24, 26, 28, 30 of the container body 12, and further defines an open top 36 bounded by the top edge of each wall section 24, 26, 28, 30. Adjacent to the top edge of each wall section 24, 26, 28, 30 the container body 12 defines an outwardly projecting rim region 38 which extends generally perpendicular to and horizontally from each wall section 24, 26, 28, 30. The rim 38 has a generally uniform height along the full length of the front and back wall sections 24, 26 of the container body 12 and near the width wise ends of the side wall side wall sections 28, 30, but defines a pair of opposing handgrip regions 40 centered on each of the side wall sections 28, 30. The height of the rim region 38 in the segment adjacent to the handgrip regions 40 is approximately equal to the thickness of the wall sections 28, 30.

Referring to FIGS. 1—3 and 5, it may be seen that the lid member 14 consists of a generally horizontal top segment 42 having a peripheral section surrounding a generally convexly curved, slightly raised central section 44, with a centrally positioned upstanding neck region 46 extending upwardly therefrom. The neck region 46 defines a generally circular waste aperture 48 and a bore extending entirely therethrough and communicating with the receptacle region 34 and waste aperture 48 when the lid member 14 is mounted on the container body 12 as shown in FIG. 1.

The handle 16 is formed from a straight section of rod (not shown) having a cross-sectional diameter, and bent to form a generally C-shape, with the opposing ends of the handle member 16 being pivotably received within a pair of recessed handle slots 50 in the sides 52 of the raised section 44 of the lid member 14. The internal side of the handle slots 50 are completely sealed as shown in FIGS. 2 and 3 so that no contaminants may leak out between the lid member 14 and handle member 16. The handle member 16 may pivot within the handle slots 50 between two lowered positions each adjacent to the raised section 44 of the lid member 14 on either side of the neck region 46 as shown in FIG. 1, and to any raised position displaced from the lowered position such as shown in FIG. 5, including a position raised directly above the waste aperture 48 and neck region 46. The raised central section 44 of the lid member 14 should extend upwardly from the surrounding peripheral section to a maximum height of no more than approximately two to three times the diameter of the rod used to form the handle member 16.

Referring to FIGS. 2, 3 and 5, it may be seen that the lid member 14 defines a depending skirt 54 which extends downwardly generally perpendicular to the lid member 14 along the edges thereof corresponding to the front wall section 26, back wall section 24, and one side wall section 30. The depending skirt 54 has a height generally equal to or slightly greater than the height of the rim region 38 along the corresponding wall sections 24, 26, 30 of the container body 12. A projecting rib member 56 extends inwardly generally perpendicular to the depending skirt 54 of the lid member 14 along the length of the depending skirt 54 corresponding to the front wall section 26, back wall section 24, and side wall section 30.

Figure 4:
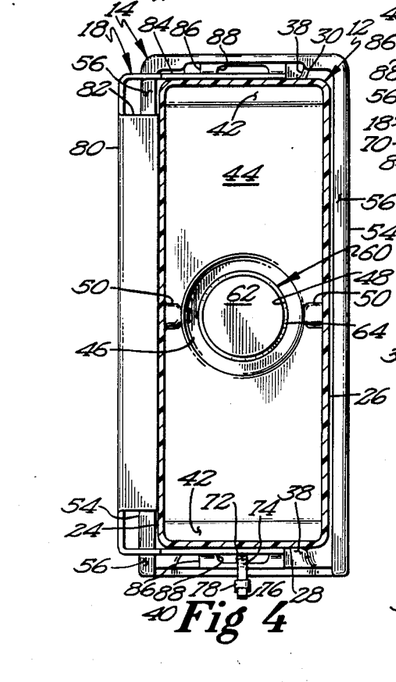
FIG. 4 is a horizontal section view of the upper end of the disposal container body and lid of this invention taken through line 4—4 of FIG. 2.

The projecting rib member 56 extends inwardly a distance or width generally equal to the distance the rim region 38 extends outwardly from the corresponding wall section 24, 26, 30, such that the rib member 56 of lid member 14 underlies and is securely engaged beneath the rim region 38 of the container body 12. The width of the rib member 56 is less in the area corresponding to the handgrip region 40 of the side wall section 30, as shown in FIG. 4, such that a user may insert his fingertips between the rib member 56 and container body 12 to assist in removing the lid member 14 from the container body 12 as described in detail below.

Referring particularly to FIG. 5, it may be seen that to mount the lid member 14 on the rim region 38 of the container body 12, the rim region 38 of the container body 12 is slidably received within and between the sections of the depending skirt 54 corresponding to the length of the lid member 14, with the rib member 54 extending from the depending skirt 56 engaging beneath the rim region 38. Thus, the end of the lid member 14 corresponding to the side wall section 28 of the container body is generally open so as to permit passage of the rim region 38 of the container body 12 therethrough.

The exposed end edges 58 of the depending skirt 54 and top segment 42 of the lid member 14 are curved or curled inwardly and downwardly, respectively, to wrap partially around the rim region 38 of the container body 12.

It is necessary in order to mount the lid member 14 on the container body 12 that the depending skirt 54 flex or bend outwardly very slightly as the front and back wall sections 24, 26 of the container body 12 pass between the rib members 56, with the depending skirt 54 then exerting pressure inwardly on the rim region 38 of the container body 12. Once the front and back wall sections 24, 26 of the container body 12 have passed completely through between the end edges 58 of the rib members 56, the depending skirt 54 may spring back into a locked or engaging position as shown in FIG. 1. In this manner, the lid member 14 may be slidably and engagingly received and mounted upon the rim region 38 of the container body 12.

The waste aperture 48 may be selectively closed and sealed by a closure plug 60 shaped and sized to be partially received through the waste aperture 48 and within the neck region 46, and to securely lodge therein to provide a substantially airtight seal between the interior receptacle region 34 and the exterior of the disposal container 10. As shown in FIGS. 3 and 5, in the case of a circular aperture 48 the closure plug 60 should preferably comprise a circular base section 62 of smaller diameter than the waste aperture 48, with a wall segment 64 extending upwardly such that the top peripheral edge 66 of the closure plug 60 has a diameter somewhat greater than the diameter of the waste aperture 48 such that the closure plug 60 may not pass completely therethrough, but will instead become securely lodged therein. The base section 62 and wall segment 64 of the closure plug are preferably formed from a thin but durable plastic to form a concave recess or cavity 68 having an open top within the closure plug 60. The plastic used to form the closure plug 60 should be both thick and durable enough to resist puncture by sharps, and yet deformable enough to permit the closure plug 60 to fit tightly within the waste aperture 48. It is understood that the closure plug 60 lodging in and contacting the waste aperture 48 forms a complete and secure seal therewith.

The disposal container 10 is preferably equipped with a pliable plastic bag or first liner 70 constructed from a thin plastic film or sheet material and defining the exterior surface of the liner 70 to completely conform to the interior surface of the container body 12 when the liner is received within the receptacle region 34 and filled with a liquid. Sufficient excess liner material may in some applications be provided so that the liner portion adjacent to the open top of the liner 70 may be folded over the rim region 38 and extend below the rim region 38 and the depending skirt 54 of the lid member 14 when the lid member 14 is mounted on the container body 12.

Preferably, a second or interior liner 71 constructed from a resilient single ply fiber board material is inserted within the first plastic liner 70. The interior liner 71 has generally rectangular shape with an enclosed bottom and an open top, a height approximately equal to the inside depth of the container body 12, and length and width dimension approximately equal to those of the base section 22. The interior liner 71 may be placed inside the plastic liner 70, and then both inserted into the receptacle region 34 of the container body 12.

Referring to FIGS. 1 and 5, it may be seen that the rim region 38 of the container body 12 corresponding to the side wall section 28 above the handgrip segment 40, as well as the lid member 14, each define a small circular aperture 72 which are aligned when the lid member 14 is mounted on the container body 12, and through which a plastic locking strip 74 may be threaded and secured. Such locking strips 74 are well known to the art for a variety of uses, and comprise a serrated web 76 and a notched clasp member 78 which permits the serrated web 76 to pass through in only one direction, thus allowing the locking strip 74 to be looped and cinched as shown in FIG. 1 and to be removed only by cutting the serrated web 76.

The mounting bracket 18 for the disposal container 10 has a generally vertical back panel 80 with a spacer 82 extending generally perpendicularly from and connected to the bottom edge of the back panel 80, as shown in FIGS. 4 and 5. The mounting bracket 18 also has a pair of securing arms 84 extending generally perpendicularly from and connected to the opposing side edges of the back panel 80 such that one of the securing arms 84 is disposed along and closely confronts the exterior surface of each of the side wall sections 28, 30 of the container body 12 when the disposal container is seated and secured within the mounting bracket 18 as shown in FIG. 1. Each securing arm 84 terminates in an outwardly projection tab 86 adjacent to the front side wall 24 of the container body 12, and each tab 86 and securing arm 84 define a slot 88 through which the serrated web 76 o the locking strip 74 may be inserted and fastened, to thereby securely retain the disposal container 10 within the mounting bracket 18. The mounting bracket 18 may be attached to any generally vertical surface using doubled sided adhesive tap strips 94 with peel-away backing 96, or with conventional threaded fasteners inserted through one or more apertures 98 in the back panel 80 of the mounting bracket 18.

In operation, a person will remove the lid member 14 from the empty container body 12 by inserting the fingertips of one hand upwardly between the rib member 56 of the depending skirt 54 and the side wall section 30 of the container body 12, and will grasp the container body 12 at the opposing side 28 with the other hand, and slidably remove the lid member 14 from the rim region.

The person will then open a plastic liner 70 and insert an interior liner 71 into that liner 70, and then insert those liners 70, 71 completely into the receptacle region 34 of the container body 12 such that the outer liner 70 contacts the base section 22 of the container body 12, and is pressed into place by the interior liner 71 and conforms generally to the interior of the receptacle region 34.

The lid member 14 is then mounted on the rim region 38 of the container body 12 by sliding the rim region 38 of the container through the open nd edge 58 of the lid member 14, which causes the depending skirt 54 to flex outwardly slightly. The rim region 38 is further inserted between the opposing sections of the depending skirt 54 and above the rib member 56 until the rim member 38 of the container body 12 is completely received within the lid member 14 such that the depending skirt springs back to its unflexed position with the rib member 56 engaged under the rim region 38 along the side wall sections 28, 30 of the container body 12 as shown in FIG. 1.

The user may thread the pointed end of the serrated web 76 of the locking strip 74 through the apertures 72 in the container body 12 and lid member 14 and insert the serrated web 76 through the clasp member 78 and cinch down the locking strip 74 such that the lid member 14 may not be moved relative to the container body 12. The excess portion of the serrated web 76 of the locking strip 74 is then cut off. The locking strip 74 may alternately be applied after the disposal container 10 is placed in a mounting bracket 18 at a remote location for use.

The closure plug 60 is then inserted into the waste aperture 48 in the neck region 46 by passing the base section 62 through the waste aperture 48 and pressing downwardly on the closure plug 60 until the wall segment 64 lodges within the waste aperture 48, and continuing said pressure to firmly engage the closure plug 60 and seal the waste aperture 48.

The disposal container 10 may then be positioned in any location convenient for use in disposing of contaminated articles (not shown) such a sharps or the like, either by resting the base section 22 on a generally flat horizontal surface, or by seating the disposal container 10 within the mounting bracket 18. The closure plug 60 may be selectively removed, or the user may remove and replace the closure plug 60 each time an article is disposed of into the disposal container 10. To remove the closure plug 60 from the waste aperture 48, the user may extend one or more fingers onto the open top of the cavity 68, and grasp the portion of the wall section 64 extending above the neck region 46, and withdraw the closure plug 60 from the waste aperture 48.

The contaminated article may then be inserted into the disposal container 10 through the waste aperture 48, and if for some reason the article does not drop completely into the receptacle region 34, the closure plug 60 may be used to tamp the article down into the receptacle region 34 such that the closure plug 60 may be replaced within the aperture, thereby maintaining the seal.

Once the disposal container has been filled with contaminated articles or material, or according to a predetermined schedule, the disposal container 10 may be removed from the mounting bracket 18 and taken to a disposal site. If an outside or centralized service is utilized for disposing of the contaminated materials, that service might choose to equip any carts or vehicles it uses to transport the disposal containers 10 with a predetermined number of the mounting brackets 18.

In order to permit carrying a plurality of the disposal containers 10 of this invention to a remote location for installation, use, or disposal, a transport case 100 may be utilized. The transport case 200 is molded from the same type of high impact plastic material as the disposal containers 10, and includes a tote container body 102 and a tote lid 104 pivotally connected to the tote container body 102 along the one of the side edges of the open top rim 110 of the tote lid 104 overlaps and rests upon the top rim 106 of the tote body 102 which is recessed or curved inward along the top edge thereof. The tote lid 104 is further secured in a closed position on top of the tote body 102 using a pair of clasps 112 attached to the side of the tote body 102 and tote lid 104 opposing the hinges 108.

Figures 7, 8, 9, 10, 11:
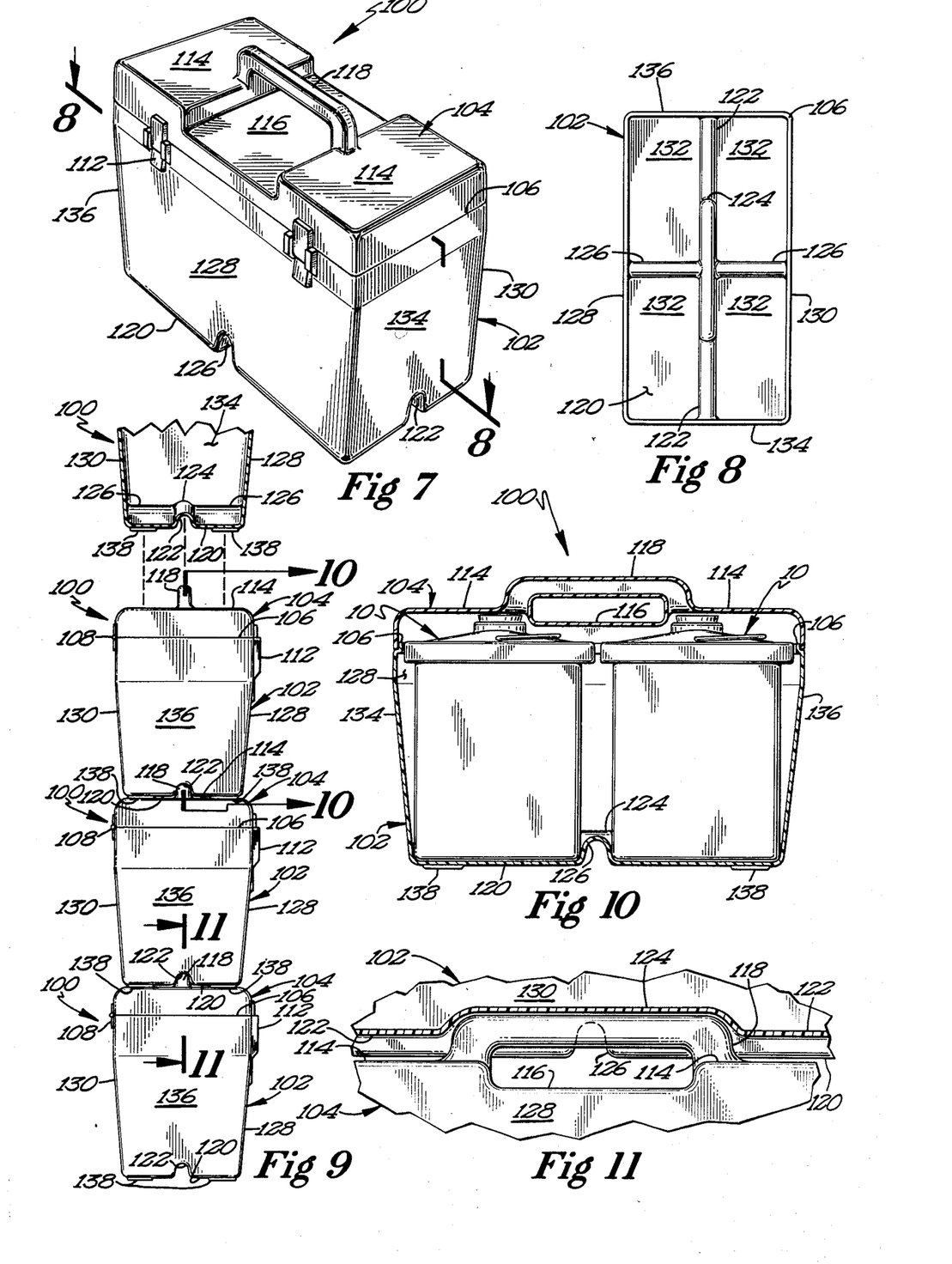
FIG. 7 is a perspective view of the transport case of this invention.
FIG. 8 is a horizontal top cross section view of the tote container portion of the transport case taken through line 8—8 in FIG. 7.
FIG. 9 is a side elevation view showing a plurality of like transport cases stacked in a vertical column, with the top transport case partially broken away.
FIG. 10 is a front cross section view of one of the transport cases taken through line 10—10 of FIG. 9 showing a pair of disposal containers received therein.
FIG. 11 is a side elevation view of two stacked transport cases with the top transport case sectioned along its longitudinal center line.

Referring to FIGS. 7 and 10, the tote lid 104 further defines a pair of opposing raised portions 114 at the opposing ends of the tote lid 104 with a lower or recessed portion 116 extending therebetween. Extending between and connected to each of the raised portions 114 is an inverted U-shaped tubular handle 118 which is displaced above the lower portion 116 of the tote lid 104.

The bottom panel 120 of the tote body 102 defines a first longitudinal channel 122 extending along the length of the tote body 102 and extending upwardly into the receptacle region thereof. The longitudinal channel is wide enough, and has is wade enough, and has a raised center portion 124 which may receive the handle 118 of a like transport case 100 therein when the transport case 100 is stacked in vertical alignment on the like transport case 100 as shown in FIGS. 9 and 11.

The tote body 102 also defines a pair of second or lateral channels 126 extending across the width of the tote body 102 generally perpendicular to the longitudinal channel 122 and between the longitudinal channel 122 and the front and back sidewalls 128, 130 of the tote body 102 and centered along the length thereof.

Together, the longitudinal channel 122 and transverse channels 126 define cross shaped walls extending upward a distance within the receptacle region of the tote body 102, thus dividing the tote body 102 into four generally rectangular compartments 132 of substantially equal size.

When one or more of the disposal containers 10 are received within the transport case 100 as shown in FIG. 10, the base section 22 of each disposal container 10 rests on the interior planar surface of the 120 bottom panel 120 of the tote body 102 within one of the compartments 132. The upwardly extending neck region 46 and closure plug 60 are disposed proximate to the inner surface of one of the raised portions 114 of the tote lid 104, and adjacent the side ends of the lower portion 116 thereof. The end edges of the disposal containers 10 in the proximity of the rim regions 38 closely confront the inner surfaces of the inwardly curved top rim 106 of the tote body 102. The end walls 134, 136 of the tote body 102 are tapered outwardly and upwardly so as to accommodate the fact that the rim region 38 of the disposal containers 10 extend outwardly a distance from the respective walls sections 24, 26, 28, 30. The transport case 100 may also include a plurality of foot pads 138 attached to or integrally molded onto the outer surface of the bottom panel 120 to stabilize the transport cases 100 when stacked or freestanding.

Once the disposal container has been delivered to the disposal cite, a technician will determine what types of materials or contaminants may be contained within the disposal container based upon any labels, written records, or according to some other compilation supplied by the user. The technician will also determine the best or most suitable means for disposing of the waste material, or the disposal facility may be equipped such that all waste materials are treated in a similar and satisfactory manner.

The technician will then cut the locking strip 74, and remove the lid member 14 as described above. The liners 70, 71 and their contents may then be removed for treatment and disposal, or the entire disposal container 10 may be sterilized or treated with the contents therein, and the contents then removed. Once the contents are removed, the disposal container is thoroughly cleaned, and new liners 70, 71 are inserted into the container body 12 and the disposal container 10 is reassembled as previously described. The disposal container 10 may then be returned to a facility for continued use.

Various other embodiments of the disposal container 10 of this invention may be designed and constructed, such as forming a lid member 14 for the disposal container 10 having a snap-on engagement with the rim 38 of the container body 12 whereby projections and corresponding recesses on either the rim 38 or lid member 14 will engage and secure the lid member 14 to the container body 12.

While the preferred embodiment of the above disposal container 10 and transport case 100 have been described in detail above with references to the attached drawing figures, it is understood that various changes and adaptations may be made therein without departing from the spirit and scope of the appended claims.

What is claimed is:

1. A disposal container for containing and transporting contaminated materials, said disposal container comprising:
   a container body, said container body having a base and a plurality of upright walls extending upwardly from said base, said upright walls forming a pair of opposing sides and a pair of opposing ends of said container body, said body defining a receptacle region having a depth and a generally rectangular open top bounded by a rim, said rim having a projecting region extending a distance outwardly in a generally horizontal direction from said upright walls of said container body;
   a first and a second liner, said liners being removably insertable within said receptacle region of said container body;
   a lid member, said lid member being slidably and engagingly mountable on said container body such that at least a portion of said lid member extends over and above each part of said projecting region of said rim, and such that at least a portion of said lid member extends under said projecting region of said rim along said opposing sides, said lid member further defining a waste aperture extending entirely through said lid member and communicating with said receptacle region when said lid member is mounted on said container body, said waste aperture having a shape and being sized to receive the contaminated material therethrough; and
   closure means for selectively closing said waste aperture.

2. The disposal container of claim 1 wherein said first liner is constructed from a thin sheet material and defines an interior region, an open top, and an exterior surface.

3. The disposal container of claim 2 wherein the second liner is constructed from a generally resilient material and is selectively inserted within the first liner, said second liner being generally rectangular in shape and having an enclosed bottom and an open top, said second liner further having a height approximately equal to the depth of the receptacle region such that said second liner may be received within the first liner and the first and second liners than slidably inserted into the receptacle region of the container body, said second liner causing said first liner to conform generally to the shape of the receptacle region and remain upright within the receptacle region.

4. The disposal container of claim 1 wherein each of the sides of the container body have a length, and the portion of the lid member which extends under the rim of the container body when the lid member is mounted on the container body extends along substantially the entire said length of each of the sides of the container body.

5. The disposal container of claim 4 wherein the portion of the lid member which extends under the rim of the container body when the lid member is mounted on the container body projects inwardly a distance generally equal to or less than the distance which the projecting portion of the rim extends outwardly from the upright walls of the container body, the portion of the lid member which extends under the rim further defining a pair of opposing tabs, each said tab extending inwardly a distance greater than the distance which the projecting portion of the rim extends outwardly from the upright walls of the container body, each said tab positioned adjacent to one of the ends of the container body.

6. The disposal container of claim 1 wherein the lid member defines a depending skirt portion connected to and extending between the portion of the lid member which extends over and above the rim of the container body and the portion of the lid member which extends under the rim of the container body when the lid member is mounted on the container body.

7. The disposal container of claim 6 wherein the lid member is mounted on the container body by passing the lid member onto the rim of the container body from one of the ends of the container body along substantially the entire length of the side of the container body to the opposing end of the container body, such that the rim of the container body is slidably received between the portion of the lid member which extends over and above each part of the rim and the portion of the lid member which extends under the rim.

8. The disposal container of claim 1 wherein the lid member defines a first aperture and the container body defines a second aperture, said first aperture being adjacent to and aligned with said second aperture when the lid member is mounted on the container body, said disposal container further comprising:
   a locking strip, said locking strip having a length and a width such that said locking strip may be threaded through the first and the second apertures and secured so as to prevent the lid member from being removed from the container body.

9. The disposal container of claim 8 wherein the locking strip evidences when removal of the lid member from the container body is attempted.

10. The disposal container of claim 1 wherein a portion of the lid member extends under the rim along one of the ends of the container body.

11. The disposal container of claim 10 wherein the portion of the lid member which extends under the rim along one of the ends of the container body further defines a handgrip region.

12. The disposal container of claim 11 wherein the portion of the lid member which extends under the rim along one of the ends of the container body extends inwardly a distance generally equal to the distance which the projecting portion of the rim extends outwardly from the upright wall of the container body, and wherein the portion of the lid member which extends under the rim along the handgrip region is spaced apart a distance from the upright wall of the container body.

13. The disposal container of claim wherein the lid member further comprises:
a generally upstanding neck region, said upstanding neck region defining a bore extending therethrough and communicating with the receptacle region and the waste aperture when the lid member is mounted on the container body, said bore having a shape and being sized to receive the contaminated material therethrough.

14. The disposal container of claim 1 wherein the closure means comprises:
a plug, said plug having a base portion sized so as to pass through the waste aperture, and a tapered wall section extending upwardly and generally outwardly from said base and having a cross sectional shape substantially the same as the shape of the waste aperture such that said wall section may be securely lodged within the waste aperture to seal the waste aperture.

15. The disposal container of claim 14 wherein the plug further defines a concave recessed region opposing the waste aperture when the plug is inserted into the waste aperture.

16. The disposal container of claim 1 which may be mounted to a generally vertical surface, said disposal container further comprising:
a mounting bracket, said mounting bracket having a pair of arms, each arm being disposed on one of the ends of the disposal container and including means for supporting the disposal container from beneath the rim region thereof, said mounting bracket further having a back panel connected to and extending between each said arm, and
means for fastening said mounting bracket to the generally vertical surface.

17. The disposal container of claim 16 wherein the mounting bracket further comprises:
a spacer connected to and extending from the back panel of the mounting bracket a distance approximately equal to the distance the projecting region of the rim projects outwardly from the side wall of the container, said spacer contacting the side wall of the disposal container closely confronting the back panel of the mounting bracket when the disposal container is mounted therein, said spacer maintaining the disposal container in a substantially vertical direction without substantial tilting.

18. The disposal container of claim 1 wherein the lid member has a center section and a perimeter section surrounding the center section, said center section having a generally convex curve and being raised slightly relative to said perimeter section.

19. The disposal container of claim 18 further comprising:
a handle member being constructed from a rod member having a diameter, said rod member being formed into a generally C-shape and having a pair of opposing ends, the center section of the lid member being raised from the perimeter section a distance sufficient to accommodate attaching the opposing ends of said handle member to the center section, said distance the center section is raised not exceeding about three times the diameter of the rod member from which the handle is formed.

20. The disposal container of claim 18 wherein the raised center section defines a pair of recesses, and wherein the handle member is formed into a gnerally C-shape having a pair of opposing ends, each of said opposing ends being pivotably received within one of said recesses in the raised center section of the lid member.

21. The disposal container of claim 1 further comprising:
a handle member, said handle member being pivotably connected to the lid member.

* * * * *